United States Patent [19]

Mabille

[11] 4,156,157

[45] May 22, 1979

[54] ALTERNATE CONSTANT CURRENT OR VOLTAGE GENERATOR FOR AN ULTRASONIC GENERATOR

[75] Inventor: Pierre Mabille, Bordeaux, France

[73] Assignee: Societe Satelec, Talence, France

[21] Appl. No.: 906,554

[22] Filed: May 16, 1978

[30] Foreign Application Priority Data

May 18, 1977 [FR] France .............................. 77 15247

[51] Int. Cl.² ........................................... H01L 41/10
[52] U.S. Cl. ................................................ 310/316
[58] Field of Search ................................ 310/314–319

[56] References Cited

U.S. PATENT DOCUMENTS

| 3,443,130 | 5/1969 | Shoh | 310/316 |
| 3,526,792 | 9/1970 | Shoh | 310/316 |
| 3,586,936 | 6/1971 | McLeroy | 310/316 X |
| 3,668,486 | 6/1972 | Silver | 310/316 X |

*Primary Examiner*—Mark O. Budd
*Attorney, Agent, or Firm*—J. Harold Nissen

[57] ABSTRACT

This ultrasonic generator comprises a transducer supplied by an oscillator via a transformer. The oscillator is supplied in parallel by a constant current generator and a voltage generator. Means are also provided to block the voltage generator as long as the impedance of the load remains lower than an adjustable threshold, so that the supply functions as constant current generator and, on the contrary, to block the current generator as soon as the impedance of the load exceeds the adjustable threshold, so that the supply then functions as voltage generator and limits the output power.

4 Claims, 3 Drawing Figures

ALTERNATE CONSTANT CURRENT OR VOLTAGE GENERATOR FOR AN ULTRASONIC GENERATOR

BACKGROUND OF THE INVENTION

The present invention relates to an ultrasonic generator which may be used in particular in dentistry.

Heretofore known ultrasonic generators generally comprise power transducers of the piezoelectric or magnetostrictive type, and they may be classed in two distinct categories depending on whether the transducer used is tuned to the series frequency or the parallel frequency.

A transducer operating on its parallel frequency is characterised in that, on the one hand, its impedance attains its maximum for the parallel frequency and, on the other hand, an increase in the mechanical load provokes a reduction in the impedance.

Certain constructors use this solution as it enables a good adaptation of power in load to be obtained by means of a voltage supply. However, the principal drawback of the circuits using a transducer tuned to the parallel frequency is that it is necessary to apply on the transducer very high voltages even for applications of moderate power. This renders this solution unsuitable for medical applications or for very high power industrial applications.

The functioning of a transducer tuned to the series frequency is the opposite of that of a transducer tuned to the parallel frequency. In fact, a transducer functioning on its series frequency is characterised in that, on the one hand, its impedance attains its minimum for the series frequency and, on the other hand, an increase in the mechanical load provokes an increase in the impedance.

There again, numerous known apparatus use, for the transducer tuned to the series frequency, a variable voltage supply for controlling the ultrasonic oscillator. However, this solution has the drawback of causing the transducer to operate irrationally and dangerously. In fact, the consequence of this type of supply is that the power furnished to the transducer decreases, as a function of the impedance of said latter, according to a hyperbolic law and therefore the greater the mechenical work required, the less the generator furnishes power, which is totally illogical. What is most serious with such a solution, is that, when the transducer is no longer charged, the power which is applied thereto tends towards the infinite, which, in practice, may be translated by a breakdown of the ultrasonic tool.

It is seen from the above that the voltage supply systematically opposes the functioning of a transducer tuned to its series frequency.

Attemps have already been made to remedy this drawback by using complex massive circuits tuned to the series frequency of the transducer. However, these solutions present in turn the drawback of leading to bulky circuits, of requiring very precise passive components, which are therefore not easily reproducible, and of being able to function only on one frequency.

SUMMARY OF THE INVENTION

The present invention aims at remedying the drawbacks of the known generators by providing a completely reliable circuit which automatically adapts itself to the effective mechanical work of the transducer and which may control transducers of any frequency.

To this end, this ultrasonic generator comprising a transducer supplied by an oscillator via a transformer, is characterised in that the oscillator is supplied in parallel by a constant current generator and a voltage generator and in that means are provided to block the voltage generator as long as the impedance of the load remains lower than an ajustable threshold, so that the supply functions as constant current generator and, on the contrary, to block the current generator as soon as the impedance of the load exceeds the adjustable threshold, so that the supply then functions as voltage generator and limits the output power.

BRIEF DESCRIPTION OF THE DRAWINGS

The invention will be more readily understood on readirig the following description with reference to the accompanying drawings, in which.

DESCRIPTION OF THE PREFERRED EMBODIMENT

Figure 1:
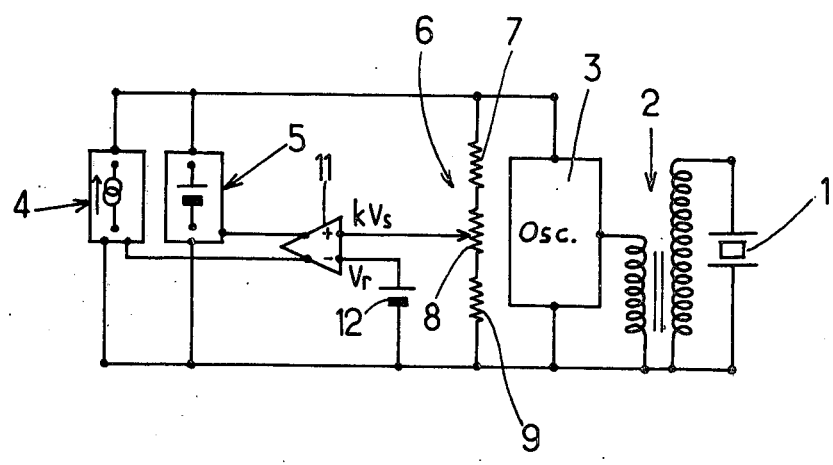
FIG. 1 is a block diagram of an ultrasonic generator according to the invention.

Refferring to the drawings, the ultrasonic generator shown in FIG. 1 comprises an ultrasonic transducer 1 of the piezoelectric type, which is connected to the terminals of the secondary winding of a transformer 2. The primary winding of this transformer is connected to the output of an oscillator 3.

According to the invention, the oscillator 3 is supplied in parallel by a constant current generator 4 and a voltage generator 5. In addition, means are provided for blocking the voltage geneator 5 as long as the impedance of the load remains lower than an adjustable threshold and on the contrary for blocking the current generator 4 as soon as this impedance exceeds the above-mentioned adjustable threshold. These means comprise a voltage divider 6 connected in parallel on the oscillator 3 and the generators 4 and 5, this voltage divider comprising, in series, a resistor 7, a potentiometer 8 and a resistor 9. The cursor of the potentiometer 8 is connected to an input of an error amplifier 11, the other input of which receives a fixed reference voltage furnished by a constant voltage source 12. The error amplifier 11 is in its turn connected, by two outputs, to the constant current generator 4 and the voltage generator 5 respectively.

Thus, the error amplifier 11 permanently compares a fraction $kV_s$ of the input voltage $V_s$ with the fixed reference voltage $V_r$ furnished by the source of voltage 12.

Figure 2:
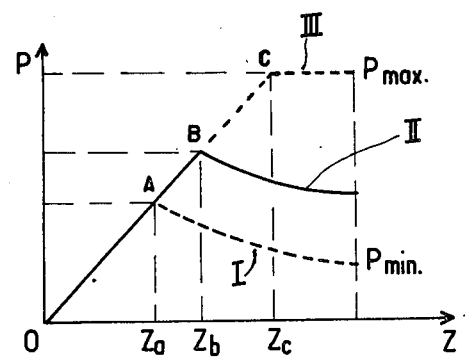
FIG. 2 is a diagram illustrating the functioning of the generator according to the invention.

As long as the fraction $kV_s$ of the input voltage $V_s$ is lower than the reference voltage $V_r$, the comparing amplifier 11 blocks the voltage generator 5 and the constant current generator 4 intervenes alone for the supply of the oscillator 3. In this case, the power supplied to the transducer 1 is proportional to its impeance, therefore to the mechanical work demanded. This is shown in the diagram of FIG. 2 which shows the variation in the power supplied P as a function of the impedance Z of the transducer 1, in the case of a minimum power (curve I), an intermediate power (curve II) and maximum power (curve III) respectively. The power furnished is adjustable by means of the potentiometer 8 of the voltage divider 6. If the curve II corresponding to the intermediate power is considered, it is seen that, as long as the impedance Z of the transducer 1 remains lower than the threshold $Z_b$, the power P supplied to the transducer varies proportionally to the impedance, according to straight section OB. For the minimum and maximum powers, the impedance thresholds are $$Z_a < Z_b \text{ and } Z_c > Z_b$$

respectively.

If the fraction $kV_s$ becomes higher than the reference voltage $V_r$, the comparing amplifier 11 changes state and then causes the blocking of the constant current generator 4. The supply then functions as voltage generator and limits the output power.

FIG. 2 shows, in fact, if the curve II corresponding to the intermediate power is considered, that, when the impedance Z exceeds the threshold $Z_b$, the power P reduces when the impedance Z increases according to a hyperbolic law which is the usual characteristic obtained in apparatus using solely a voltage generator. Consequently, when the impedance Z attains and exceeds the adjustable impedance threshold $Z_b$, the power P cannot exceed the maximum value corresponding to point B since, after this point, it decreases progressively. Thus, the apparatus according to the invention is completely reliable since, according to the conditions of adjustment, the power cannot exceed a determined maximum value. If the apparatus is used, for example, for dental scaling, it is absolutely certain, when using the apparatus according to the invention, that the ultrasonic tool will destroy the tartar without attacking the tooth.

Figure 3:
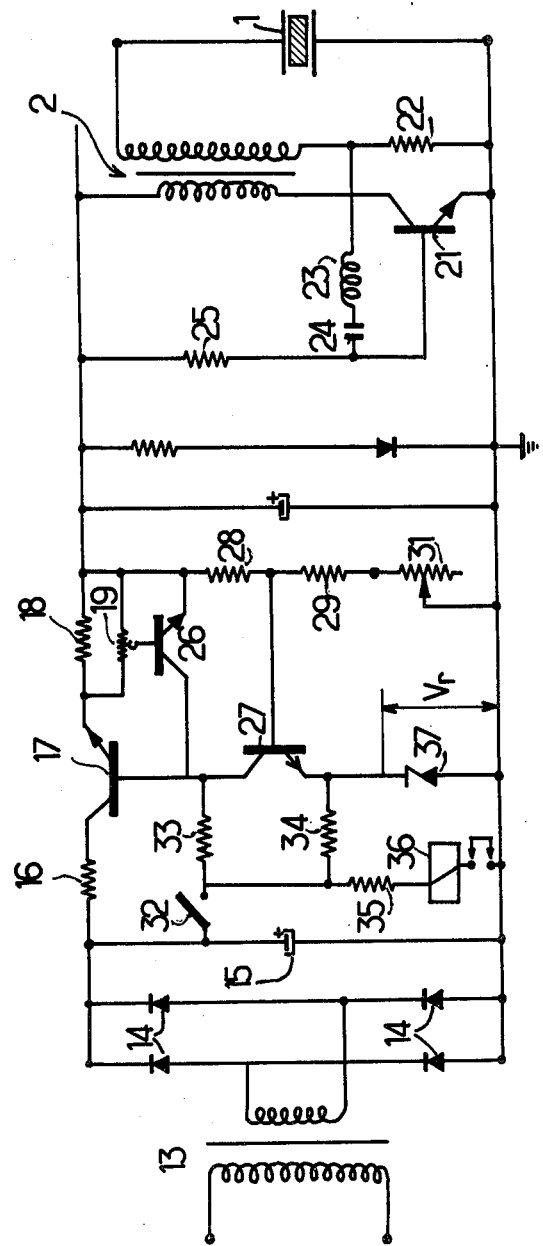
FIG. 3 is an electrical diagram of an embodiment of the invention.

A non-limiting embodiment of the invention will now be described with reference to FIG. 3. The component elements shown therein, similar to those of FIG. 1, are given the same references.

The ultrasonic generator according to the invention comprises an input transformer 13 whose primary winding is connected to the A.C. mains and the secondary winding of which supplies a rectifier bridge comprising an assembly of diodes 14 and a filtering capacitor 15 in parallel. The positive terminal of the D.C. supply thus produced is connected by a resistor 16 to the collector of a ballast transistor 17 whose emitter is connected, via a resistor 18 and a potentiometer 19 in parallel, to one end of the primary winding of the transformer 2. The other end of this primary winding is connected to the collector of a transistor 21 whose emitter is connected to earth. One end of the secondary winding of the transformer 2 is connected to the transducer 1 whilst the other end is connected on the one hand to earth, via a resistor 22 and on the other hand to the base of the transistor 21 via a circuit comprinsing, in series, an inductance 23 and a capacitor 24. A resistor 25 is also connected between the base of the transistor 21 and the point of junction between the resistor 18 and the primary winding of the transformer 2. The transistor 21 thus functions as self-oscillator due to a current feedback made by the resistor 22, inductance 23, capacitor 24 and resistor 25 assembly.

The supply circuit of this oscillator will now be more particularly described. This circuit comprises, in addition to the ballast transistor 17, two other transistors 26 and 27 whose collectors are connected together to the base of the ballast transistor 17. The base of the transistor 26 is connected to the cursor of the potentiometer 19 whilst its emitter is connected on the one hand to the point of junction between the resistor 18 and the primary winding of the transformer 2, and on the other hand to a series assembly comprising a resistor 28, a resistor 29 and a potentiometer 31 whose cursor is earthed. A normally open actuating switch 32 is connected between the positive terminal and the resistors 33, 34 and 35, the resistor 33 also being connected to the base of the ballast transistor 17 and to the collector of the two transistors 26, 27, the resistor 34 being connected to the emitter of the transistor 27 and finally the resistor 35 being connected to a relay 36. Finally, the emitter of the transistor 27 is connected to earth via a Zener diode 37 constituting the source of reference voltage.

The functioning of the generator which has just been described is as follows: the ballast transistor 17 functions, according to the working conditions, as constant current generator or as voltage generator.

It will firstly be assumed that the transducer 1 functions off-circuit. In this case, the current absorbed by the oscillator comprising the transistor 21 tends to become very considerable, this bringing about an increase in the drop in voltage at the terminals of the series resistor 18. This increase in the voltage drop then provokes the passage of the transistor 26 to the conducting state, this tending to block the ballast transistor 17. This results in a limitation of the increase of current previously assumed. The assembly formed by the transistor 17, the resistor 18, the potentiometer 19 and the transistor 26 therefore functions as constant current generator. The value of this current is adjusted by means of the potentiometer 19. Under these conditions, the supply furnishes a power adapted in optimal manner to the work of the transducer 1.

It will now be assumed that the transducer furnishes very considerable mechanical work, which is translated by an increase in the impedance of the oscillator. Since the supply furnishes, through the ballast transistor 17, a constant current, the supply voltage will increase but this voltage supply is transmitted on the base of the transistor 27 by the divider bridge constituted by the resistors 28, 29 and the potentiometer 31.

As soon as the voltage at the point of junction of the resistors 28, 29, which is applied to the base of the transistor 27, becomes higher than the reference voltage $V_r$ suplied by the Zener diode 37 increased by 0.7 volt, the transistor 27 becomes conducting and tends to block the ballast transistor 17, this having for its effect to limit the supply voltage to the value:

$$V = (R_{28} + R_{29} + R_{31}/R_{29} + R_{31})(V_r + 0.7)$$

The ballast transistor 17 then functions as stabilised voltage supply. Under these conditions, the power in the transducer 1 is limited and may even decrease if too considerable a mechanical work is demanded of the transducer.

What I claim is:

1. In an ultrasonic generator comprising a transducer supplied by an oscillator via a transformer, the oscillator is supplied in parallel by a constant current generator and a voltage generator and means are provided to block the voltage generator as long as the impedance of the load remains lower than an adjustable threshold, so that the supply functions as constant current generator and, on the contrary, to block the constant current generator as soon as the impedance of the load exceeds the adjustable threshold, so that the supply then functions as voltage generator and limits the output power.

2. The generator of claim 1, further comprising means for for comparing a fraction $kV_s$ of the output voltage $V_s$ with a reference voltage $V_r$ so as to block the voltage generator as long as the fraction $kV_s$ of the output voltage is lower than the reference voltage $V_r$ and to block the current generator when it becomes higher than this reference voltage.

3. The generator of claim 2, further comprising a voltage divider branched in parallel on the oscillator and comprising an adjustable potentiometer, a source of reference voltage, and a comparing amplifier whose two inputs are respectively connected to the cursor of the potentiometer and to the source of reference voltage and the outputs and which are respectively connected to the constant current generator and to the voltage generator, in order to unblock one of these generators by blocking the other, according to the functioning conditions.

4. The generator of claim 3, further comprising a ballast transistor connected, via a resistor and a potentiometer in parallel, to one end of the primary winding of the transformer supplying the transducer, a second transistor whose base is connected to the cursor of the potentiometer, the emitter to one end of a voltage divider bridge comprising two resistors and potentiometer in series, this bridge being connected in parallel on the oscillator, and a third transistor whose base is connected to a point of the voltage divider bridge and the emitter to a source of reference voltage, the collectors of the second and third transistors being connected to the base of the first ballast transistor.

* * * * *